United States Patent [19]

Schneider et al.

[11] Patent Number: 4,520,210

[45] Date of Patent: May 28, 1985

[54] PREPARATION OF CONCENTRATED AQUEOUS SOLUTIONS OF QUATERNIZATION PRODUCTS OF TERTIARY AMINOALKYL ESTERS OR TERTIARY AMINOALKYLAMIDES OF ACRYLIC OR METHACRYLIC ACID

[75] Inventors: Kurt Schneider, Bad Durkheim; Wilfried Heide, Erpolzheim; Juergen Hartmann, Ludwigshafen; Heinrich Hartmann, Limburgerhof, both of Fed. Rep. of Germany

[73] Assignee: BASF Aktiengesellschaft, Ludwigshafen, Fed. Rep. of Germany

[21] Appl. No.: 556,409

[22] Filed: Nov. 30, 1983

[30] Foreign Application Priority Data

Nov. 30, 1982 [DE] Fed. Rep. of Germany ....... 3244274

[51] Int. Cl.³ .................. C07C 93/193; C07C 103/70
[52] U.S. Cl. .............................. 560/222; 260/501.15; 560/218
[58] Field of Search .............................. 560/222, 218; 260/501.15; 564/296

[56] References Cited

U.S. PATENT DOCUMENTS

| | | | |
|---|---|---|---|
| 3,661,880 | 5/1972 | Markert et al. | 526/305 |
| 3,948,979 | 4/1976 | Patterson | 560/222 |
| 4,362,890 | 12/1982 | Ohshima et al. | 560/222 |

*Primary Examiner*—Natalie Trousof
*Assistant Examiner*—L. Hendriksen
*Attorney, Agent, or Firm*—Oblon, Fisher, Spivak, McClelland & Maier

[57] ABSTRACT

Concentrated aqueous solutions of quaternization products of tertiary aminoalkyl esters or tertiary aminoalkylamides of acrylic or methacrylic acid are prepared by reaction of the corresponding esters or amides with an alkylating agent in a water-soluble ketone as solvent, by a process wherein, in order to isolate the quaternization product, an amount of water is added to the reaction mixture such that two phases form, and the lower aqueous phase, which contains the quaternization product in solution, is separated from the upper phase, which contains the ketone and residual alkylating agent.

6 Claims, No Drawings

PREPARATION OF CONCENTRATED AQUEOUS SOLUTIONS OF QUATERNIZATION PRODUCTS OF TERTIARY AMINOALKYL ESTERS OR TERTIARY AMINOALKYLAMIDES OF ACRYLIC OR METHACRYLIC ACID

German Published Application DAS No. 2,848,627 discloses a process for the preparation of a liquid, directly polymerizable mixture of acrylamide and quaternization products of tertiary aminoalkyl esters or tertiary aminoalkylamides of acrylic or methacrylic acid. The alkylating agent is allowed to act on the mixture, which contains from 30 to 80% by weight of acrylamide. The resulting melt has a melting point which is not below 50° C. Such melts are difficult to handle industrially because transport lines and pumps have to be heated to above the melting point of the mixtures.

It is an object of the present invention to provide a process for the preparation of concentrated aqueous solutions of quaternization products of tertiary aminoalkyl esters or tertiary aminoalkylamides of acrylic or methacrylic acid by reaction of the corresponding esters or amides with an alkylating agent in a water-soluble ketone as solvent, wherein the resulting aqueous solutions of the quaternization products are easy to handle, do not contain any other monomers and can be employed directly in the polymerization.

We have found that this object is achieved, in accordance with the invention, by a process wherein, in order to isolate the quaternization product, an amount of water is added to the reaction mixture such that two phases form, and the lower aqueous phase, which contains the quaternization product in solution, is separated from the upper phase, which contains the ketone and residual alkylating agent. The amount of water added to the reaction mixture in this process is such that a 50–95% strength by weight aqueous solution of the quaternization product is formed. The resulting concentrated aqueous solution of the basic monomers is so pure that it can be used, without an additional purification step, directly in polymerizations for the preparation of homopolymers or copolymers.

In general, tertiary aminoalkyl esters or tertiary aminoalkylamides of acrylic acid or methacrylic acid can be employed in the quaternization reaction. Particularly important compounds for the preparation of homopolymers and copolymers are, for example, di-$C_1$-$C_2$-alkylamino-$C_2$-$C_6$-alkyl acrylates and the corresponding methacrylates, as well as di-$C_1$-$C_2$-alkylamino-$C_2$-$C_6$-alkylacrylamides and the corresponding methacrylamides. Examples of suitable starting materials for the quaternization reaction are dimethylaminoethyl acrylate, dimethylaminoethyl methacrylate, diethylaminoethyl acrylate, diethylaminoethyl methacrylate, dimethylaminopropyl acrylate, dimethylaminopropyl methacrylate, diethylaminopropyl acrylate, diethylaminopropyl methacrylate, dimethylaminoisopropyl acrylate, dimethylaminoisopropyl methacrylate, dimethylamino-n- or -isobutyl acrylate, dimethylamino-n- or -isobutyl methacrylate, dimethylamino-n-pentyl acrylate, dimethylamino-n-pentyl methacrylate, dimethylaminoneopentyl acrylate, dimethylaminoneopentyl methacrylate, dimethylaminohexyl acrylate and dimethylaminohexyl methacrylate, as well as the corresponding basic acrylamides and methacrylamides, such as ethylacrylamide, diethylaminoethylmethacrylamide, dimethylaminopropylacrylamide, dimethylaminopropylmethacrylamide, dimethylaminoisopropylacrylamide, dimethylaminoisopropylmethacrylamide, diethylaminoisopropylacrylamide, diethylaminoisopropylmethacrylamide, dimethylamino-n- or -isobutylacrylamide, dimethylamino-n- or -isobutylmethacrylamide, diethylamino-n-butylacrylamide, dimethylaminoneopentylacrylamide, dimethylaminoneopentylmethacrylamide, dimethylaminohexylacrylamide and dimethylaminohexylmethacrylamide.

Suitable alkylating agents are alkyl halides, the choice of alkylating agent being restricted only in that the resulting quaternization product must be soluble in water. Examples of suitable alkylating agents are methyl chloride, methyl bromide, methyl iodide, ethyl chloride, ethyl bromide, ethyl iodide, butyl chloride, butyl bromide and benzyl chloride. Methyl chloride is preferably used for the quaternization of the basic esters or amides.

Since the quaternization products of tertiary aminoalkyl esters or tertiary aminoalkylamides of acrylic acid or methacrylic acid, in contrast to the non-quaternized products, are solid crystalline substances, the reaction has to be carried out using a diluent which is liquid at room temperature, so that thorough mixing of the components is ensured during the reaction. The solvents used are ketones which are liquid at room temperature, eg. acetone, methyl ethyl ketone, diethyl ketone, methyl isopropyl ketone and diisopropyl ketone, acetone or methyl ethyl ketone being preferably used. The quaternization reaction of the relevant basic esters or amides in acetone is a prior art procedure. The quaternization can be carried out within a wide temperature range, for example at from room temperature to 200° C. If the temperature employed is above the boiling point of the solvent, the reaction is carried out in an autoclave. Where methyl chloride is used as the quaternizing agent, it is also advisable to carry out the reaction at elevated temperatures under superatmospheric pressure. The reaction with methyl chloride in acetone is preferably carried out at from 20° to 150° C., preferably from 40° to 100° C. It is of course also possible to carry out the quaternization at room temperature by passing methyl chloride into a solution of the basic ester or amide of acrylic acid or methacrylic acid in a ketone. The concentration of the basic ester or amide of acrylic or methacrylic acid in a ketone, or in a mixture of ketones, is from 5 to 80, preferably from 20 to 60, % by weight. Regardless of the conditions under which it is carried out, the quaternization gives solid products which are insoluble in acetone or the other water-soluble ketonic solvents. The concentration of the starting materials in the ketones is chosen so that the resulting reaction mixture is also stirrable.

To isolate the quaternization product, water is added to the reaction mixture, whereupon, surprisingly, two phases form. This state of affairs could not be foreseen, since it was to be assumed that the water-miscible ketones and the water-soluble quaternization product would form a homogeneous solution. The amount of water added to the reaction mixture is such that a 50–95, preferably 75–85, % strength by weight aqueous solution of the quaternization product is formed. The lower aqueous phase contains the quaternization product in dissolved form as well as a small amount of water-soluble ketone. The resulting aqueous solution of the quaternization product is sufficiently pure to be employed, without an additional purification step, directly in polymerization reactions. The upper phase is formed after water has been added to the reaction mixture, and contains the ketone and, where relevant, the residual alkylating agent. In the alkylation, the molar ratio can vary within a substantial range. For example, from 1 to 3, preferably from 1 to 1.5, moles of alkylating agent are used per mole of the compound quaternized. The novel process has the advantage, which should not be underrated, that the upper phase, which essentially consists of the ketone and the unreacted alkylating agent, can be re-used directly in the quaternization reaction without any working up step having to be carried out. The ketones used as solvents can be anhydrous or, if they have already been used in the novel process, can contain as much as 5% by weight of water. Of course, the water content depends on the particular ketone used. Preferably, the ketone is anhydrous or contains not more than 1% by weight of water. In order to avoid premature polymerization of the basic monomers during the quaternization reaction, it is advisable to carry out the quaternization at very low temperatures and, if necessary, also in the presence of a polymerization inhibitor.

It is sufficient to state that lower temperatures require relatively long reaction times and higher temperatures short reaction times, and that the process can be carried out either continuously or batchwise.

The concentrated aqueous solutions obtained according to the invention are used directly as monomers for the preparation of polymers. They can be used to prepare either homopolymers or copolymers. Of particular importance are copolymers of acrylamide with dimethylaminoethyl acrylate, of acrylamide with dimethylaminoethyl methacrylate, of acrylamide with dimethylaminoethylacrylamide and of acrylamide with dimethylaminoethylmethacrylamide, as well as the corresponding copolymers of diethylaminoethyl acrylate with acrylamide and/or methacrylamide, the basic monomers being prepared according to the invention and being present in quaternized form, preferably as methochlorides. The copolymers can furthermore contain acrylic acid or methacrylic acid as copolymerized units, and are preferably used as flocculants in the dewatering of sludge and the treatment of waste water.

In the Examples which follow, parts and percentages are by weight.

EXAMPLE 1

5.53 kg of acetone, 1.29 kg of dimethylaminoethyl acrylate and, as a stabilizer, 1.3 g of hydroquinone monomethyl ether are initially taken in an autoclave which has a capacity of 10 liters and can be stirred. The autoclave is then closed, and the stirred contents are heated to 50° C. At this temperature, 0.97 kg of methyl chloride is forced in continuously at a rate such that the pressure in the autoclave is about 3 bar. When the addition of the methyl chloride is complete, the reaction mixture is allowed to continue reacting for a further 3 hours at 50° C. and is then cooled to room temperature. Thereafter, 0.75 kg of water is added to the reaction mixture and stirring is continued for another half an hour. After the stirrer has been switched off, the mixture separates into an upper, organic phase of 5.50 kg and a lower, aqueous phase of 2.50 kg which is colorless, contains about 15% by weight of acetone and, in solution, the dimethylaminoethyl acrylate quaternized with methyl chloride, and can be used as a monomer directly in polymerization reactions.

EXAMPLE 2

1,094 g of anhydrous acetone, 200 g of dimethylaminoethyl acrylate and 0.2 g of hydroquinone monomethyl ether are initially taken in a kettle equipped with a stirrer, and the stirred mixture is heated to 55° C. 152 g of ethyl bromide are then added in the course of 2 hours, after which the reaction mixture is stirred for a further 12 hours at 55° C. and then cooled to 25° C. Thereafter, 784 g of water are added to the reaction mixture, the latter is stirred for 15 minutes and the stirrer is then switched off. 416 g of an aqueous phase are obtained which contains the quaternized dimethylaminoethyl acrylate in solution. The aqueous solution can be used as a monomer phase directly in the polymerization.

EXAMPLE 3

1,165 g of acetone, containing 0.2% by weight of water, and 200 g of dimethylaminoethyl acrylate and 0.2 g of hydroquinone monomethyl ether are initially taken in a kettle equipped with a stirrer, and the mixture is heated to 60° C. The reaction mixture is stirred, and 177 g of benzyl chloride are added dropwise in the course of 1 hour. The reaction is complete after 15 hours at 60° C. The reaction mixture is left to cool, water is added until 2 phases have formed, and 487 g of an aqueous solution are then separated off. This aqueous solution contains the benzylated dimethylaminoethyl acrylate hydrochloride and can be used directly in the polymerization.

PREPARATION OF POLYMERS

A. Water-in-oil polymer emulsions
General method of preparation:

The components of the oil phase, whose composition is shown in Table 1, are mixed in a vessel provided with a stirrer, a thermometer and a nitrogen inlet and outlet. The aqueous monomer phase, whose composition is also shown in Table 1, is then stirred into this mixture. Nitrogen is passed through the emulsion for 30 minutes, and the emulsion is then heated to 50° C. in the course of 15 minutes. At this temperature, a solution of the initiator in a little acetone (cf. Table 1 for type and amount) is added. The temperature of the emulsion is kept at 50°–55° C. for 2 hours, after which the same amount of the polymerization initiator is once again added and polymerization is continued for 2 hours at 55° C. A coagulate-free water-in-oil polymer emulsion which does not settle out is obtained.

TABLE 1

| Composition of the water-in-oil emulsions | | Example 4 | Comparative Example 1 | Example 5 | Comparative Example 2 |
| --- | --- | --- | --- | --- | --- |
| Oil phase: | | | | | |
| Hydrocarbon mixture (boiling range 192–254° C.[1] | [g] | 260 | 260 | 235 | 235 |
| Emulsifier (reaction product obtained from 1 mole of oleyl glycidyl ether, 1 mole of glycerol and 2 moles of ethylene oxide) | [g] | 25 | 25 | 25 | 25 |

TABLE 1-continued

| Composition of the water-in-oil emulsions | | Example 4 | Comparative Example 1 | Example 5 | Comparative Example 2 |
|---|---|---|---|---|---|
| Reaction product obtained from 1 mole of nonyl-phenol and 10 moles of ethylene oxide | [g] | 5 | 5 | — | — |
| Monomer phase: | | | | | |
| Distilled water | [g] | 140 | 185 | 190 | 325 |
| 70% strength aqueous solution of the metho-chloride of dimethylaminoethyl acrylate, obtained as described in Example 1 | [g] | 150 | — | 450 | — |
| Methochloride of dimethylaminoethyl acrylate, powder, free of acetone | [g] | — | 105 | — | 315 |
| 50% strength aqueous acrylamide solution | [g] | 390 | 390 | 70 | 70 |
| 40% strength aqueous solution of pentasodium diethylenetriaminepentaacetate | [g] | 0.23 | 0.23 | 0.04 | 0.04 |
| 37.5% strength sulfuric acid | [g] | 0.38 | 0.38 | 0.38 | 0.38 |
| Formic acid | [g] | 0.30 | 0.30 | — | — |
| 2,2'-Azobis(2,4-dimethylvaleronitrile), 30% strength in acetone | [ml] | 2 × 0.25 | 2 × 0.25 | 2 × 0.29 | 2 × 0.29 |

[1] Mixture of 84% of saturated aliphatic hydrocarbons and 16% of naphthenic hydrocarbons B. Bead polymers prepared by reverse suspension polymerization General method:

800 ml of cyclohexane and 1.1 g of a copolymer of dicyclopentadiene, maleic anhydride and styrene are initially taken in a 2 liter round-bottomed flask provided with a dropping funnel, a stirrer, a reflux condenser and a connection to a vacuum pump. The contents of the flask are heated to 50° C. and the pressure is reduced so that the mixture boils at this temperature. A mixture of the monomer solution described in the Examples and Comparative Examples below with the particular initiator solution stated therein is then added dropwise to the flask in the course of one hour. Immediately before the addition, the mixture is freed from residual oxygen by flushing with nitrogen. When the addition of the monomers is complete, polymerization is continued for one hour at about 50° C., vapor cooling being continued. The pressure is then equilibrated, and 5 ml of a 2.5% strength aqueous solution of hydroxylammonium sulfate, mixed with 0.95 ml of a 10% strength sodium hydroxide solution, are added to the suspension. A reflux condenser with a water separator is then mounted on the round-bottomed flask, and the water present in the polymer particles is removed by azeotropic distillation under atmospheric pressure. The resulting bead polymers, which have a diameter of about 0.5 mm, are filtered off and dried in a drying oven under reduced pressure at 40° C.

EXAMPLE 6

Composition of the monomer solution:

120 g of water, 61.5 g of a 70% strength aqueous solution of dimethylaminoethyl acrylate which is quaternized with methyl chloride and is obtained as described in Example 1, 63 g of acrylamide, 0.3 g of pentasodium diethylenetriaminepentaacetate and 60 mg of formic acid. The initiator solution used comprises 8.8 ml of a 3% strength solution of 2,2,-azobis(2-aminopropane)dihydrochloride in water.

EXAMPLE 7

Composition of the monomer solution:

52 g of water, 198 g of a 70% strength aqueous solution of dimethylaminoethyl acrylate which is quaternized with methyl chloride and prepared as described in Example 1, 15 g of acrylamide, 0.1 mg of pentasodium diethylenetriaminepentaacetate and 40 mg of formic acid.

The initiator solution used comprises 3.3 ml of a 3% strength aqueous solution of 2,2'-azobis(2-amidinopropane)dihydrochloride.

COMPARATIVE EXAMPLE 3

Composition of the monomer solution:

138 g of water, 43 g of crystalline dimethylaminoethyl acrylate which is quaternized with methyl chloride and does not contain any acetone, 63 g of acrylamide, 0.3 mg of pentasodium diethylenetriaminepentaacetate and 60 mg of formic acid.

The initiator solution used is that described in Example 6.

COMPARATIVE EXAMPLE 4

Composition of the monomer solution:

111 g of water, 139 g of crystalline dimethylaminoethyl acrylate which is quaternized with methyl chloride and is free of acetone, 15 g of acrylamide, 0.1 g of pentasodium diethylenetriaminepentaacetate and 40 mg of formic acid.

The initiator solution used is that described in Example 7.

Test of the performance of the polymers

In order to test the efficiency of the polymers described in Examples 4 and 5 and in Comparative Examples 1 and 2, the water-in-oil polymer emulsions are converted to aqueous polymer solutions by a method in which each emulsion is stirred into water which contains 2%, based on the polymer emulsion, of a nonylphenol which has been reacted with 10 moles of ethylene oxide. Thereafter, an amount of water is added to bring the polymer content of the aqueous solution to 0.1%. The performance of these solutions is tested with a digested sludge from a municipal sewage treatment plant. The amount of flocculant which has to be added to the sludge in order to achieve optimum flocculation is determined. The flocculation is assessed visually.

In the case of the polymers of Example 4 and Comparative Example 1, 200 mg of polymer per liter of sludge are required in each case for optimum flocculation. The same amount is required in the case of the polymers obtained as described in Example 5 and Comparative Example 2. This means that the basic monomers obtained as described in Example 1 which contain impurities, in particular acetone, from their preparation, give polymers which have the same activity as those obtained using the corresponding pure, acetone-free basic monomers.

Using the same digested sludge, the flocculating efficiency of the polymers prepared as described in Examples 6 and 7 and Comparative Examples 3 and 4 is tested. For optimum flocculation, which is assessed visually, 200 mg of polymer per liter of sludge are required in each case.

TABLE 2

| Polymer of | Composition | K value[1] | Flocculation test |
|---|---|---|---|
| Example 6 | 60% of acrylamide/40% of DEA—EA—CH$_3$Cl[2] | 219 | 200 g/m$^3$ |
| Comparative Example 3 | 60% of acrylamide/40% of DEA—EA—CH$_3$Cl | 217 | 200 g/m$^3$ |
| Example 7 | 10% of acrylamide/90% of DEA—EA—CH$_3$Cl | 210 | 200 g/m$^3$ |
| Comparative Example 4 | 10% of acrylamide/90% of DEA—EA—CH$_3$Cl | 212 | 200 g/m$^3$ |

[1] determined according to H. Fikentscher, Cellulose Chemie 13 (1932), 58–64 and 71–74, on a 0.1% strength solution in a 5% strength aqueous sodium chloride solution at 20° C.; K = $\overline{K} \cdot 10^3$
[2] DEA—EA—CH$_3$Cl = dimethylaminoethyl acrylate quaternized with methyl chloride.

We claim:

1. A process for the preparation of a concentrated aqueous solution of a quaternization product of a tertiary aminoalkyl ester or tertiary aminoalkylamide of acrylic or methacrylic acid by reaction of the corresponding ester or amide with an alkylating agent in a water-soluble ketone as solvent, wherein, in order to isolate the quaternization product, an amount of water is added to the reaction mixture such that two phases form, and the lower aqueous phase, which contains the quaternization product in solution, is separated from the upper phase, which contains the ketone and residual alkylating agent.

2. A process as claimed in claim 1, wherein an amount of water is added to the reaction mixture such that a 50–95% strength by weight aqueous solution of the quaternization product is formed.

3. A process as claimed in claim 1, wherein a di-$C_1$-$C_2$-alkylamino-$C_2$-$C_6$-alkyl acrylate or the corresponding methacrylate is quaternized with an alkyl chloride in acetone.

4. A process as claimed in claim 1, wherein a di-$C_1$-$C_2$-alkylamino-$C_2$-$C_6$-alkylacrylamide or the corresponding methacrylamide is quaternized with an alkyl chloride.

5. A process as claimed in claim 1, wherein dimethylaminoethyl acrylate is quaternized with methyl chloride.

6. A process as claimed in claim 1, wherein diethylaminoethyl acrylate is quaternized with methyl chloride.

* * * * *